(12) United States Patent
Hsiung et al.

(10) Patent No.: US 11,547,310 B2
(45) Date of Patent: *Jan. 10, 2023

(54) AUTONOMOUS FULL SPECTRUM BIOMETRIC MONITORING

(71) Applicant: VIAVI Solutions Inc., San Jose, CA (US)

(72) Inventors: Changmeng Hsiung, Redwood City, CA (US); Lan Sun, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/301,521

(22) Filed: Apr. 6, 2021

(65) Prior Publication Data

US 2021/0219857 A1    Jul. 22, 2021

Related U.S. Application Data

(63) Continuation of application No. 16/210,740, filed on Dec. 5, 2018, now Pat. No. 11,000,198.

(51) Int. Cl.
*A61B 5/021* (2006.01)
*A61B 5/024* (2006.01)
*A61B 5/00* (2006.01)

(52) U.S. Cl.
CPC .......... *A61B 5/02416* (2013.01); *A61B 5/021* (2013.01); *A61B 5/7225* (2013.01); *A61B 5/7246* (2013.01)

(58) Field of Classification Search
CPC ... A61B 5/02416; A61B 5/021; A61B 5/7225; A61B 5/7246
See application file for complete search history.

(56) References Cited

U.S. PATENT DOCUMENTS 11,000,198 B2 * 5/2021 Hsiung ................. A61B 5/021
2010/0022627 A1   1/2010 Scherer
(Continued)

OTHER PUBLICATIONS

Chang C-C., et al., "MW-PPG Sensor: An On-Chip Spectrometer Approach", Sensors, Aug. 26, 2019, vol. 19(17), 3698, 16 pages, XP055657845.
(Continued)

*Primary Examiner* — Ankit D Tejani
*Assistant Examiner* — Joshua Brendon Solomon
(74) *Attorney, Agent, or Firm* — Harrity & Harrity, LLP

(57) ABSTRACT

A device may obtain raw heartbeat data associated with a plurality of wavelength channels. The device may generate, based on a feature vector transformation, a plurality of feature vectors, each corresponding to a respective one of the plurality of wavelength channels. The device may identify a set of selected feature vectors, from the plurality of feature vectors, based on a plurality of squares of correlation coefficients, each associated with a respective pair of the plurality of feature vectors. The device may generate, based on a principal component analysis, an average feature vector of the set of selected feature vectors. The device may determine initial heartbeat cycle data based on the average feature vector. The device may correct heartbeat cycle gaps in the initial heartbeat cycle data in order to determine final heartbeat cycle data.

20 Claims, 9 Drawing Sheets

(56) References Cited

U.S. PATENT DOCUMENTS

| | | |
|---|---|---|
| 2011/0246123 A1 | 10/2011 | Dellostritto et al. |
| 2017/0245767 A1 | 8/2017 | Ferber et al. |
| 2018/0085040 A1* | 3/2018 | Ferber .................. A61B 5/7278 |
| 2020/0129130 A1 | 4/2020 | Korhonen et al. |
| 2020/0178819 A1 | 6/2020 | Hsiung et al. |
| 2021/0022633 A1* | 1/2021 | Ma ......................... A61B 5/746 |

OTHER PUBLICATIONS

Extended European Search Report for Application No. EP19213969.9, dated Feb. 3, 2020, 12 pages.

Lewandowska M., et al., "Measuring Pulse Rate With A Webcam, A Non-contact Method for Evaluating Cardiac Activity", Computer Science and Information Systems (FEDCSIS), Federated Conference, Sep. 1, 2011, pp. 405-410, XP055658550.

Sun Y., et al., "Photoplethysmography Revisited: From Contact to Noncontact, From Point to Imaging", IEEE Transactions on Biomedical Engineering, Mar. 1, 2016, vol. 63 (3), pp. 463-477, XP055658426.

* cited by examiner

AUTONOMOUS FULL SPECTRUM BIOMETRIC MONITORING

RELATED APPLICATION

This application is a continuation of U.S. patent application Ser. No. 16/210,740, filed Dec. 5, 2018, which is incorporated herein by reference in its entirety.

BACKGROUND

Photoplethysmography (PPG) is an optical technique that can be used to detect volumetric changes in blood in peripheral circulation (as blood volume changes due to the pumping action of the heart). PPG is a non-invasive method that makes measurements at the surface of the skin (e.g., at a fingertip, a wrist, an ear lobe, and/or the like). A PPG device may take the form of a multispectral sensor device (e.g., a binary multispectral (BMS) sensor device) that provides heartbeat time-series data associated with multiple wavelength channels (e.g., 64 wavelength channels). The multispectral sensor device includes multiple sensor elements (e.g., optical sensors, spectral sensors, and/or image sensors), each to receive one of the multiple wavelength channels (via a respective region of a multispectral filter) in order to capture the heartbeat time-series data.

SUMMARY

According to some implementations, a method may include: obtaining, by a device, raw heartbeat data associated with a plurality of wavelength channels; generating, by the device and based on a feature vector transformation, a plurality of feature vectors, each corresponding to a respective one of the plurality of wavelength channels; identifying, by the device, a set of selected feature vectors, from the plurality of feature vectors, based on a plurality of squares of correlation coefficients, each associated with a respective pair of the plurality of feature vectors; generating, by the device and using a principal component analysis, an average feature vector of the set of selected feature vectors; determining, by the device, initial heartbeat cycle data based on the average feature vector; and correcting, by the device, heartbeat cycle gaps in the initial heartbeat cycle data in order to determine final heartbeat cycle data to permit a biometric monitoring action to be performed.

According to some implementations, a device may include one or more memories, and one or more processors, communicatively coupled to the one or more memories, to: obtain raw heartbeat data associated with a plurality of wavelength channels; generate, based on a feature vector transformation, a plurality of feature vectors, each corresponding to a respective one of the plurality of wavelength channels; identify a set of selected feature vectors, from the plurality of feature vectors, based on a plurality of squares of correlation coefficients, each associated with a respective pair of the plurality of feature vectors; generate, based on a principal component analysis, an average feature vector of the set of selected feature vectors; determine initial heartbeat cycle data based on the average feature vector; and correct heartbeat cycle gaps in the initial heartbeat cycle data in order to determine final heartbeat cycle data to permit a biometric monitoring action to be performed.

According to some implementations, a non-transitory computer-readable medium may store instructions, the instructions including one or more instructions that, when executed by one or more processors, cause the one or more processors to: obtain raw heartbeat data associated with a plurality of wavelength channels; generate, based on a feature vector transformation, a plurality of feature vectors, each corresponding to a respective one of the plurality of wavelength channels; identify a set of selected feature vectors, from the plurality of feature vectors, based on a plurality of squares of correlation coefficients, each associated with a respective pair of the plurality of feature vectors; generate, based on a principal component analysis, an average feature vector of the set of selected feature vectors; determine initial heartbeat cycle data based on the average feature vector; and correct heartbeat cycle gaps in the initial heartbeat cycle data in order to determine final heartbeat cycle data to permit a biometric monitoring action to be performed.

DETAILED DESCRIPTION

The following detailed description of example implementations refers to the accompanying drawings. The same reference numbers in different drawings may identify the same or similar elements.

As described above, a multispectral sensor device may be capable of measuring, obtaining, collecting, or otherwise determining heartbeat time-series data associated with multiple (e.g., 16, 32, 64, and/or the like) wavelength channels. Such data is herein referred to as raw heartbeat data. In practice the raw heartbeat data can be quite noisy, and can include frequent baseline shifts. Due to such noise and/or baseline shifts, segmenting the raw heartbeat data into systolic phases (e.g., times during which the heart is contracting) and diastolic phases (e.g., times during which the heart is resting) can be difficult or impossible. Thus, it is often difficult or impossible to use the raw heartbeat data in association with performing a biometric monitoring action, such as performing vital sign monitoring (e.g., determining an instantaneous heart rate, determining a blood pressure, and/or the like) since the raw heartbeat data may lead to inaccurate, unreliable results.

Some implementations described herein provide a heartbeat cycle data device for determining, based on raw heartbeat data collected by a multispectral sensor device, heartbeat cycle data based on which a biometric monitoring action can be performed. More specifically, some implementations described provide a heartbeat cycle data device capable of processing the raw heartbeat data in order to determine the heartbeat cycle data (e.g., data identifying start and end times of heartbeat cycles), thereby allowing a biometric monitoring action that uses the heartbeat cycle data to provide a comparatively more accurate and/or comparatively more reliable result (e.g., as compared to using raw heartbeat data in association with performing the biometric monitoring action).

Figure 1A:
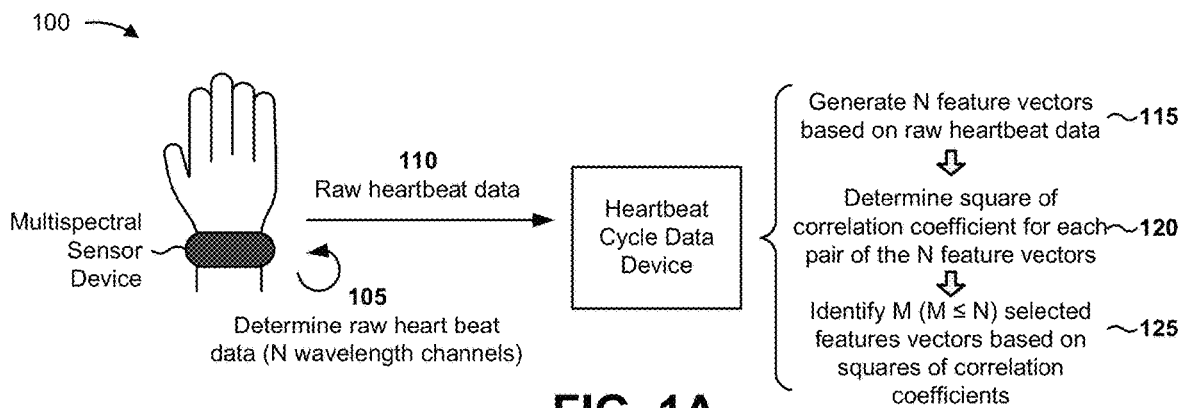
FIGS. 1A and 1B are diagrams of an example implementation described herein.
Figure 1B:
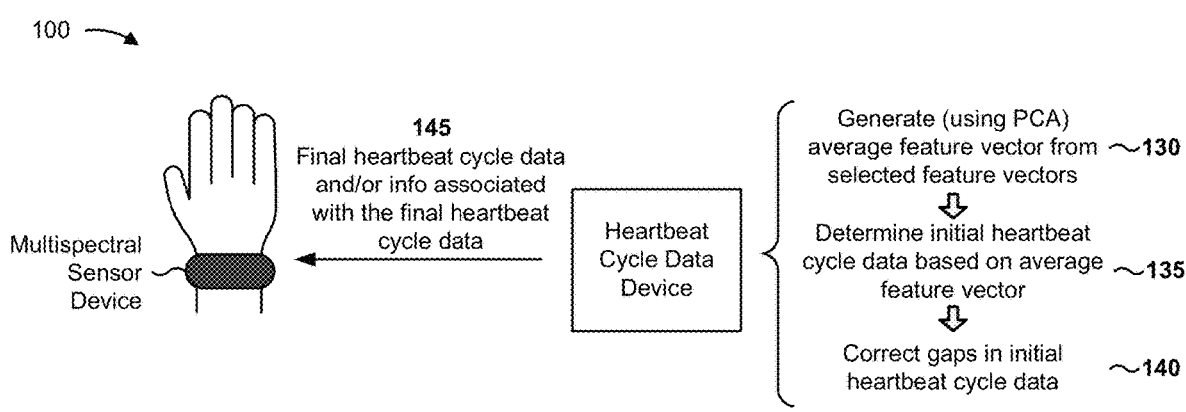

FIGS. 1A and 1B are diagrams of an example implementation 100 described herein.

As shown in FIG. 1A, a multispectral sensor device may be positioned relative to a skin surface of a subject. For example, as shown in FIG. 1A, the multispectral sensor device may be a device worn on the wrist of the subject. In some implementations, the multispectral sensor device may be positioned relative to the skin surface at another location on the body, such as on a fingertip, an arm, a leg, an ear lobe, and/or the like. In some implementations, the multispectral sensor device includes a BMS sensing device that operates in, for example, the visible (VIS) spectrum, the near infrared (NIR) spectrum, and/or the like.

As shown by reference number 105, the multispectral sensor device may determine (e.g., measure, gather, collect, and/or the like) raw heartbeat data associated with N (N>1) wavelength channels. The raw heartbeat data includes, for each of the N wavelength channels, photometric response data that indicates a blood volume beneath the skin surface (at the location of the multispectral sensor device) at a given time point.

As shown by reference number 110, a heartbeat cycle data device may obtain the raw heartbeat data from the multispectral sensor device. The heartbeat cycle data device is a device capable of determining heartbeat cycle data based on the raw heartbeat data associated with multiple wavelength channels, as described herein. In some implementations, the heartbeat cycle data device may be integrated with the multispectral sensor device (e.g., in a same package, a same housing, on a same chip, and/or the like). Alternatively, the heartbeat cycle data device may be separate (e.g., remotely located) from the multispectral sensor device.

In some implementations, the heartbeat cycle data device may obtain the raw heartbeat data in real-time or near real-time (e.g., when the multispectral sensor device is configured to provide the raw heartbeat data as the multispectral sensor device obtains the raw heartbeat data). Additionally, or alternatively, the heartbeat cycle data device may obtain the raw heartbeat data based on the multispectral sensor device (e.g., automatically) providing the raw heartbeat data on a periodic basis (e.g., every one second, every five seconds, and/or the like). Additionally, or alternatively, the heartbeat cycle data device may obtain the raw heartbeat data from the multispectral sensor device based on requesting the raw heartbeat data from the multispectral sensor device.

As shown by reference number 115, the heartbeat cycle data device may generate N feature vectors, each corresponding to a respective one of the N wavelength channels, based on the raw heartbeat data. For example, the heartbeat cycle data device may perform a feature vector transformation on items of raw heartbeat data associated with each of the N wavelength channels in order to generate N feature vectors.

The systolic and diastolic phases of heartbeat cycles are characterized by upward sloping and downward sloping portions, respectively, of signals representing the raw heartbeat data. Thus, if such characteristics are captured in feature vectors that are generated from transforming the raw heartbeat data, signal to noise ratios (SNRs) will be improved (e.g., as compared with the raw heartbeat data). In some implementations, moving quarter-period slopes feature vectors may be generated for this purpose. In some implementations, such a feature vector transformation mitigates noise originated from point-to-point variations, while providing sufficient range to capture a number of time steps before the feature vector changes sign.

In some implementations, a quarter-period moving windows slopes feature vector may be generated using the following equation:

$$FV=(R_t-R_0)/R_0$$

where $R_t$ is a photometric response, identified by the raw heartbeat data, at a current time step and $R_0$ is a photometric response, identified by the raw heartbeat data, wFV time steps before the current time step. Here, wFV is a quarter of an estimated heartbeat cycle period of the subject (e.g., a typical heartbeat cycle period, an average heartbeat cycle period, a previously determined heartbeat cycle period, and/or the like, which can be adjustable). Notably, while wFV is described as being a quarter (¼) of the heartbeat cycle period of the subject, wFV can be different than ¼ of the heartbeat cycle period (e.g., ⅙ of the heartbeat cycle period, ⅕ of the heartbeat cycle period, ⅓ of the heartbeat cycle period, ½ of the heartbeat cycle period, and/or the like), in some implementations. Examples illustrating feature vector generation are described below with regard to FIGS. 5A-5D.

In practice, not all wavelength channels will have an acceptable SNR during operation of the multispectral sensor device and, as a result, the heartbeat cycle data device may need to filter feature vectors corresponding to these noisy wavelength channels. In some implementations, the heartbeat cycle data device may perform such filtering based on squares of correlation coefficients of the N feature vectors. A lower square of a correlation coefficient (e.g., closer to 0) indicates that two variables are less correlated, while a higher square of a correlation coefficient indicates that two variables are comparatively more highly correlated. Thus, as shown by reference number 120 in FIG. 1A, the heartbeat cycle data device may determine squares of correlation coefficients for each pair of the N feature vectors.

As shown by reference number 125, the heartbeat cycle data device may identify M (M≤N) selected feature vectors based on the squares of the correlation coefficients. In some implementations, each of the selected feature vectors may correspond to a respective clean wavelength channel. As an example, the heartbeat cycle data device may determine N×(N−1)/2 squares of the correlation coefficients, each associated with one pair of the N feature vectors. Next, the heartbeat cycle data device may identify a set of M×(M−1)/2 squares of the correlation coefficients, of the N×(N−1)/2 determined squares of the correlation coefficients, that satisfy a threshold (e.g., a minimum allowable value, such as 0.80, 0.90, 0.95, and/or the like). Here, the heartbeat cycle data device may identify a set of M selected feature vectors that correspond to the set of M×(M−1)/2 squares of the correlation coefficients that satisfy the threshold. In this way, the heartbeat cycle data device may filter wavelength channels with an unacceptable amount of noise.

As shown in FIG. 1B, and by reference number 130, after identifying the M selected feature vectors, the heartbeat cycle data device may generate, using a principal component analysis (PCA), an average feature vector of the M selected feature vectors. For example, since data segmentation may be designed to be performed on univariate time-series data, the multivariate time-series data, corresponding to the M selected feature vectors, may need to be compressed into univariate time-series data. This compression can be viewed as an averaging of the M selected feature vectors. In some implementations, the average feature vector is generated based on a first principal component (PC1) determined as a result of the PCA. In some implementations, generating the average feature vector using a PCA allows systolic and diastolic phases of heartbeats to be more readily identified (e.g., since the average feature vector will have a higher SNR than an individual one of the set of selected feature vectors or a mean of the set of selected feature vectors, as described below). An example illustrating such an average feature vector is described below with regard to FIG. 6.

As shown by reference number 135, the heartbeat cycle data device may determine initial heartbeat cycle data based on the average feature vector. The initial heartbeat cycle data may include information that identifies a start time and an end time for an initial set of heartbeats. In some implementations, the heartbeat cycle data device may determine the initial heartbeat cycle data based on the average feature vector. For example, the heartbeat cycle data device may identify positive phases of the average feature vector (e.g., windows of time during which the average feature vector has a substantially positive slope and crosses a threshold value, such as zero) and negative phases of the average feature vector (e.g., windows of time during which the average feature vector has a substantially negative slope and crosses the threshold value). In this example, a positive phase (indicating the systolic phase of a heartbeat) being adjacent to a negative phase (indicating the diastolic phase of the heartbeat) defines one heartbeat cycle period, and start and end times of the heartbeat cycle can be determined accordingly. In some implementations, the heartbeat cycle data device may determine initial heartbeat cycle data that identifies start and end times for multiple heartbeats.

As further shown in FIG. 1B, and by reference number 140, the heartbeat cycle data device may correct heartbeat cycle gaps in the initial heartbeat cycle data in order to determine final (e.g., gap-free) heartbeat cycle data.

A heartbeat cycle gap may be an error, inaccuracy, inconsistency, and/or the like, in the initial heartbeat cycle data that results in a given heartbeat cycle period being identified as significantly shorter or longer than is reasonably possible. For example, in practice, the average feature vector may include spikes and/or noise that can over-divide a heartbeat cycle into several fragments of positive or negative phases. When this occurs, a heartbeat cycle period identified in the initial heartbeat cycle data will be significantly lower than an actual heartbeat cycle period. As a result, a biometric monitoring action that is performed based on such data may be inaccurate and/or unreliable. For example, an instantaneous heartbeat rate will show a significant positive spike in the case of an over-divided heartbeat (e.g., such that the determined instantaneous heart rate is much higher than the actual heart rate).

As another example, a sloping baseline in the average feature vector (e.g., caused by sloping baselines in the raw heartbeat data) can cause negative or positive phases to be undetected. For example, a positively sloped baseline can cause negative phases to go undetected, and a negatively sloped baseline can cause positive phases to go undetected. When this occurs, a heartbeat cycle period identified in the initial heartbeat cycle data will be significantly higher than an actual heartbeat cycle period. As a result, a biometric monitoring action that is performed based on such data may be inaccurate and/or unreliable. For example, an instantaneous heartbeat rate will have a negative spike in the case of such undetected phases (e.g., such that the determined instantaneous heart rate is much lower than the actual heart rate). In some implementations, correcting gaps in the initial heartbeat cycle data may remove the effects of over-divided heartbeat cycles and sloping baselines.

In some implementations, as a first step in correcting heartbeat cycle gaps in the initial heartbeat cycle data, the heartbeat cycle data device may identify one or more such heartbeat cycle gaps. For example, the heartbeat cycle data device may determine that a heartbeat cycle, identified by the initial heartbeat cycle data, has a period that satisfies a threshold. For example, the heartbeat cycle data device may determine that a given heartbeat cycle has a period that is less than a minimum heartbeat cycle period. In such a case, the heartbeat cycle data device may identify the presence of a gap caused by an over-divided heartbeat cycle. As another example, the heartbeat cycle data device may determine that a given heartbeat cycle has a period that is greater than a maximum heartbeat cycle period. In such a case, the heartbeat cycle data device may identify the presence of a gap caused by a sloping baseline.

In some implementations, the heartbeat cycle data device may be configured with information that identifies the threshold, and the threshold may be adjustable (e.g., by the heartbeat cycle data device, by the subject, and/or the like). For example, the heartbeat cycle data device may store or have access to information that identifies an estimated heartbeat cycle period associated with the subject (e.g., a typical heartbeat cycle period, an average heartbeat cycle period, a previously determined heartbeat cycle period, and/or the like), and maximum allowable positive and negative differences (e.g., an amount of time, a percentage, and/or the like) from the estimated heartbeat cycle period.

In some implementations, after identifying a heartbeat cycle gap, the heartbeat cycle data device may modify the initial heartbeat cycle data in order to correct the identified heartbeat cycle gap. For example, in the case of an over-divided heartbeat cycle, the heartbeat cycle data device may combine adjacent heartbeat cycles until an adjusted heartbeat cycle period is greater than or equal to the minimum heartbeat cycle period. As another example, in the case of an undetected phase, the heartbeat cycle data device may identify local troughs or peaks in the average feature vector during the heartbeat cycle period, and may divide the heartbeat cycle into two or more heartbeat cycles (e.g., such that adjusted heartbeat cycle periods of the two or more heartbeat cycles are less than or equal to the maximum heartbeat cycle period). In some implementations, the heartbeat cycle data device may correct multiple heartbeat cycle gaps in the initial heartbeat cycle data. In some implementations, data resulting from the correction of one or more heartbeat cycle gaps can be referred to as final (e.g., gap-free) heartbeat cycle data. Examples illustrating an effect of heartbeat cycle gap correction are described below with regard to FIGS. 7A and 7B.

In some implementations, the final heartbeat cycle data may permit a biometric monitoring action to be performed (e.g., by the heartbeat cycle data device, by the multispectral sensor device, or by another device). The biometric monitoring action may include, for example, vital sign monitoring (e.g., instantaneous heart rate determination, blood pressure determination, and/or the like), or another type of biometric determination and/or monitoring (e.g., blood oxygenation determination, augmentation index determination, hydration determination, and/or the like).

In some implementations, as shown by reference number 145, the heartbeat cycle data device may provide the final heartbeat cycle data and/or information associated with the final heartbeat cycle data. For example, in some implementations, the heartbeat cycle data device may provide the final heartbeat cycle data to a device configured to perform vital sign monitoring (e.g., instantaneous heart rate determination, blood pressure determination, and/or the like). As another example, in some implementations, the heartbeat cycle data device may provide the final heartbeat cycle data to a device configured to perform another type of biometric monitoring (e.g., blood oxygen saturation determination, hydration, and/or the like). In some implementations, the final heartbeat cycle data can be provided for use in a BMS PPG feature matrix based on which biometric monitoring can be performed.

In some implementations, the heartbeat cycle data device may determine an instantaneous heart rate based on the final heartbeat cycle data, and may provide (e.g., for display via a display screen of the multispectral sensor device and/or the heartbeat cycle data device) information that identifies the instantaneous heart rate. An example associated with determination of an instantaneous heart rate is described below with regard to FIG. 8.

In this way, a heartbeat cycle data device can determine heartbeat cycle data based on raw heartbeat data, collected by a multispectral sensor device, in order to permit a biometric monitoring action to be performed with increased accuracy and/or increased reliability (e.g., as compared to performing the biometric monitoring action based on the raw heartbeat data).

As indicated above, FIGS. 1A and 1B are provided merely as examples. Other examples may differ from what is described with regard to FIGS. 1A and 1B.

Figure 2:
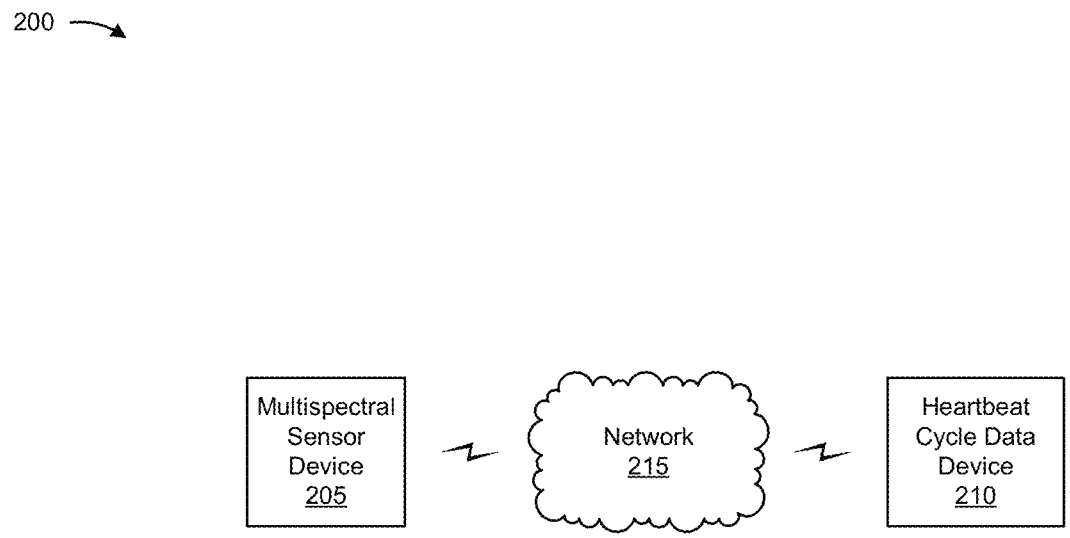
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a multispectral sensor device 205, a heartbeat cycle data device 210, and a network 215. Devices of environment 200 may interconnect via wired connections, wireless connections, or a combination of wired and wireless connections.

Multispectral sensor device 205 includes a device capable of measuring, gathering, collecting, or otherwise determining raw heartbeat data associated with a plurality of wavelength channels, as described herein. For example, multispectral sensor device 205 may include a multispectral sensing device capable of determining raw heartbeat data (in the form of multivariate time-series data) on each of 64 wavelength channels. In some implementations, multispectral sensor device 205 may operate in the visible spectrum, the near infrared spectrum, the infrared spectrum, and/or the like. In some implementations, multispectral sensor device 205 may be a wearable device (e.g., a device worn that can be worn on a wrist, a finger, an arm, a leg, a head, an ear, and/or the like). In some implementations, multispectral sensor device 205 may be integrated with heartbeat cycle data device 210 (e.g., such that multispectral sensor device 205 and heartbeat cycle data device 210 are on the same chip, in the same package, in the same housing, and/or the like). Alternatively, in some implementations, multispectral sensor device 205 may be separate from heartbeat cycle data device 210. In some implementations, multispectral sensor device 205 may receive information from and/or transmit information to another device in environment 200, such as heartbeat cycle data device 210.

Heartbeat cycle data device 210 includes a device capable of determining heartbeat cycle data based on raw heartbeat data associated with a plurality of wavelength channels, as described herein. For example, heartbeat cycle data device 210 may include an application specific integrated circuit (ASIC), an integrated circuit, a server, a group of servers, and/or the like, and/or another type of communication and/or computing device. In some implementations, heartbeat cycle data device 210 may be integrated with multispectral sensor device 205 (e.g., such that multispectral sensor device 205 and heartbeat cycle data device 210 are on the same chip, in the same package, in the same housing, and/or the like). Alternatively, in some implementations, heartbeat cycle data device 210 may be separate from multispectral sensor device 205. In some implementations, heartbeat cycle data device 210 may receive information from and/or transmit information to another device in environment 200, such as multispectral sensor device 205.

Network 215 includes one or more wired and/or wireless networks. For example, network 215 may include a wired network (e.g., when multispectral sensor device 205 and heartbeat cycle data device 210 are included in same package and/or a same chip). As another example, network 215 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
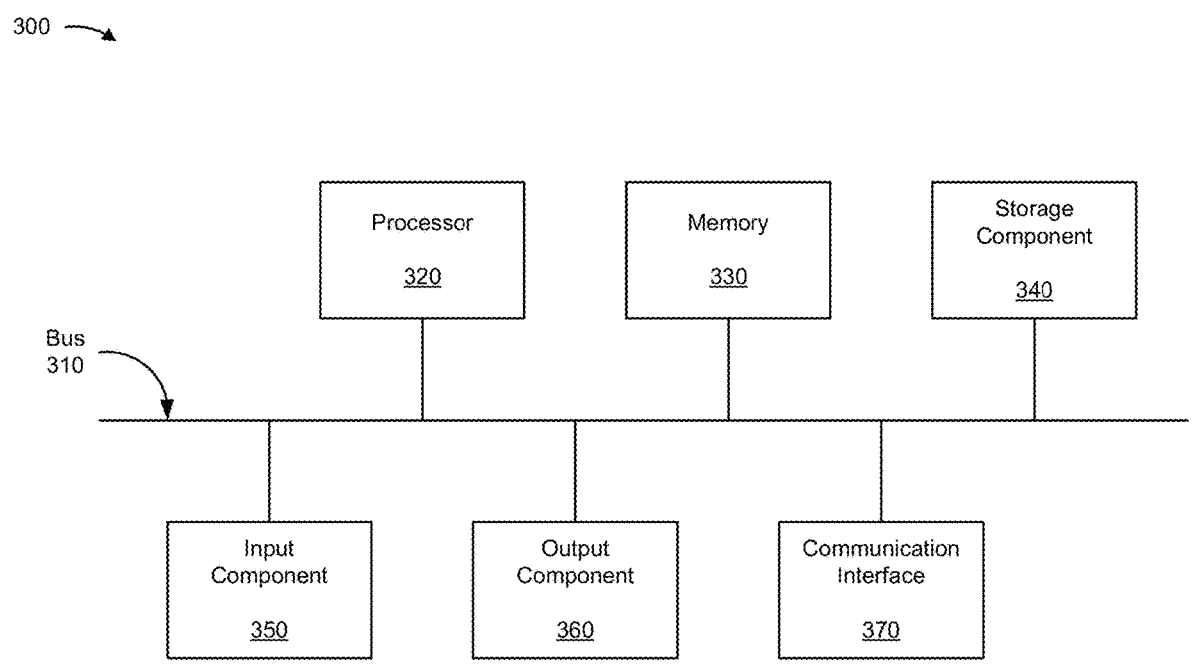
FIG. 3 is a diagram of example components of one or more devices of FIG. 2.

FIG. 3 is a diagram of example components of a device 300. Device 300 may correspond to multispectral sensor device 205 and/or heartbeat cycle data device 210. In some implementations, multispectral sensor device 205 and/or heartbeat cycle data device 210 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and/or software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
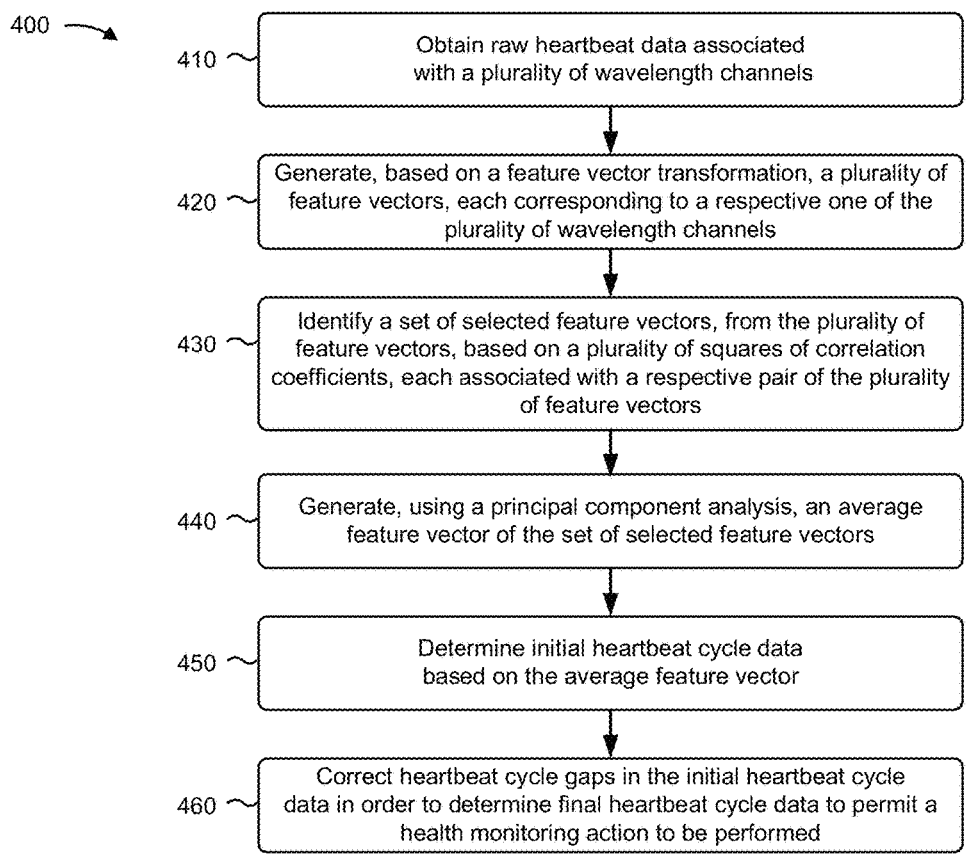
FIG. 4 is a flow chart of an example process for determining heartbeat cycle data based on raw heartbeat data associated with a plurality of wavelength channels.

FIG. 4 is a flow chart of an example process 400 for determining heartbeat cycle data based on raw heartbeat data associated with a plurality of wavelength channels. In some implementations, one or more process blocks of FIG. 4 may be performed by a heartbeat cycle data device (e.g., heartbeat cycle data device 210). In some implementations, one or more process blocks of FIG. 4 may be performed by another device or a group of devices separate from or including the heartbeat cycle data device, such as a multispectral sensor device (e.g., multispectral sensor device 205), and/or the like.

As shown in FIG. 4, process 400 may include obtaining raw heartbeat data associated with a plurality of wavelength channels (block 410). For example, the heartbeat cycle data device (e.g., using processor 320, memory 330, storage component 340, input component 350, communication interface 370, and/or the like) may obtain raw heartbeat data associated with a plurality of wavelength channels, as described above.

As shown in FIG. 4, process 400 may include generating, based on a feature vector transformation, a plurality of feature vectors, each corresponding to a respective one of the plurality of wavelength channels (block 420). For example, the heartbeat cycle data device (e.g., using processor 320, memory 330, and/or the like) may generate, based on a feature vector transformation, a plurality of feature vectors, each corresponding to a respective one of the plurality of wavelength channels, as described above.

As shown in FIG. 4, process 400 may include identifying a set of selected feature vectors, from the plurality of feature vectors, based on a plurality of squares of correlation coefficients, each associated with a respective pair of the plurality of feature vectors (block 430). For example, the heartbeat cycle data device (e.g., using processor 320, memory 330, and/or the like) may identify a set of selected feature vectors, from the plurality of feature vectors, based on a plurality of squares of correlation coefficients, each associated with a respective pair of the plurality of feature vectors, as described above.

As shown in FIG. 4, process 400 may include generating, using a principal component analysis, an average feature vector of the set of selected feature vectors (block 440). For example, the heartbeat cycle data device (e.g., using processor 320, memory 330, and/or the like) may generate, using a principal component analysis, an average feature vector of the set of selected feature vectors, as described above.

As shown in FIG. 4, process 400 may include determining initial heartbeat cycle data based on the average feature vector (block 450). For example, the heartbeat cycle data device (e.g., using processor 320, memory 330, and/or the like) may determine initial heartbeat cycle data based on the average feature vector, as described above.

As shown in FIG. 4, process 400 may include correcting heartbeat cycle gaps in the initial heartbeat cycle data in order to determine final heartbeat cycle data to permit a biometric monitoring action to be performed (block 460). For example, the heartbeat cycle data device (e.g., using processor 320, memory 330, and/or the like) may correct heartbeat cycle gaps in the initial heartbeat cycle data in order to determine final heartbeat cycle data, to permit a biometric monitoring action to be performed, as described above.

Process 400 may include additional implementations, such as any single implementation or any combination of implementations described below and/or in connection with one or more other processes described elsewhere herein.

In some implementations, the biometric monitoring action is instantaneous heart rate determination. Here, the heartbeat cycle data device may determine an instantaneous heart rate based on the final heartbeat cycle data, and provide information that identifies the instantaneous heart rate, in some implementations.

In some implementations, the biometric monitoring action is vital sign monitoring. Here, the heartbeat cycle data device may provide the final heartbeat cycle data in association with performing the vital sign monitoring.

In some implementations, the plurality of feature vectors is a plurality of moving quarter-period slopes feature vectors.

In some implementations, the heartbeat cycle data device may determine the plurality of squares of the correlation coefficients for the plurality of feature vectors, and identify a set of squares of the correlation coefficients, of the plurality of squares of the correlation coefficients, that satisfy a threshold. Here, when identifying the set of selected feature vectors, the heartbeat cycle data device may identify the set of selected feature vectors based on the set of squares of the correlation coefficients, where each of the set of squares of the correlation coefficients corresponds to a respective pair of the set of selected feature vectors.

In some implementations, the average feature vector is generated based on a first principal component associated with the principal component analysis.

In some implementations, when correcting the heartbeat cycle gaps in order to determine the final heartbeat cycle data, the heartbeat cycle data device may identify a heartbeat cycle gap based on determining that a heartbeat cycle, identified by the initial heartbeat cycle data, has a period that satisfies a threshold; and modify, based on an estimated heartbeat cycle period, the initial heartbeat cycle data in order to correct the identified heartbeat cycle gap, where a result of modifying the initial heartbeat cycle data to correct the identified heartbeat cycle gap is the final heartbeat cycle data.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5A-5D are diagrams illustrating examples of feature vectors generated based on raw heartbeat data, as described herein. Notably, identification of individual signals is not necessary for understanding the implementation illustrated by FIGS. 5A-5D; consequently, clear delineation of each signal is not shown.

Figure 5A:
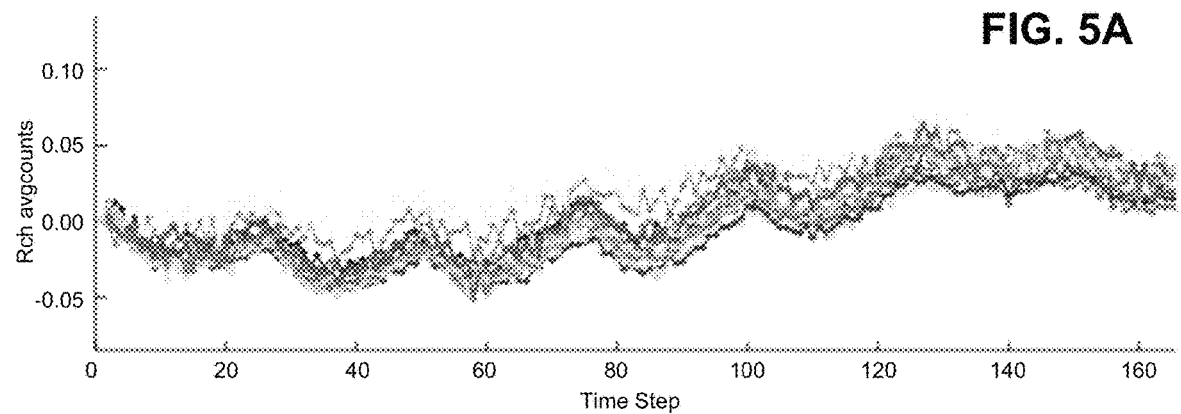
FIGS. 5A-5D are diagrams illustrating examples of feature vectors generated based on raw heartbeat data, as described herein.
Figure 5B:
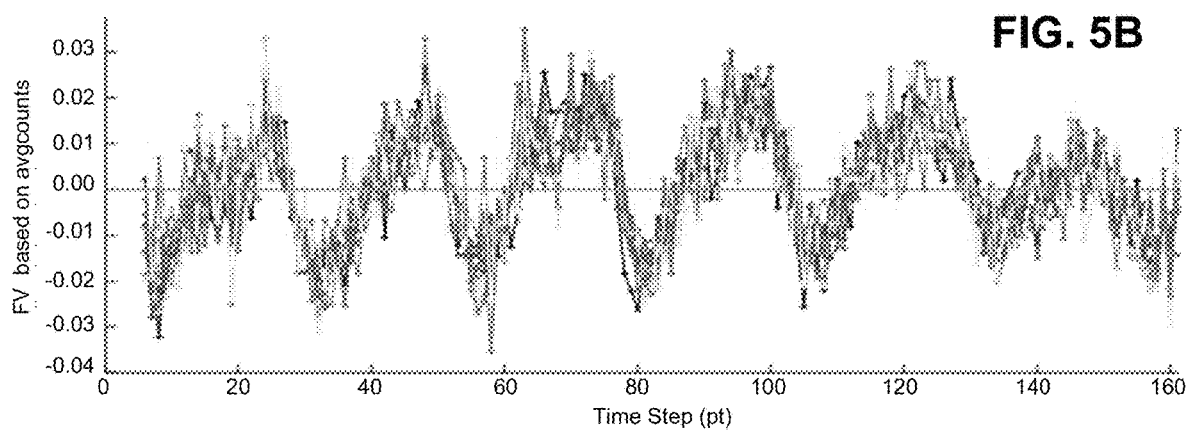

FIG. 5A is an example illustrating raw heartbeat data (in the form of relative count change of average counts) for 14 wavelength channels during a time window from time step 0 to approximately time step 180. Notably, the raw heartbeat data illustrated in FIG. 5A has a relatively flat baseline. In some implementations, as described above, feature vectors can be generated for each of the wavelength channels. FIG. 5B is an example illustrating a result of transforming the raw heartbeat data, associated with each of the 14 wavelength channels, to a respective moving quarter-period slopes feature vector. As shown in FIG. 5B, positive and negative phases of the feature vectors are readily identifiable (e.g., as compared to the raw heartbeat data). Thus, as described above, feature vector transformation may allow heartbeat cycle data to be determined by heartbeat cycle data device 210.

Figure 5C:
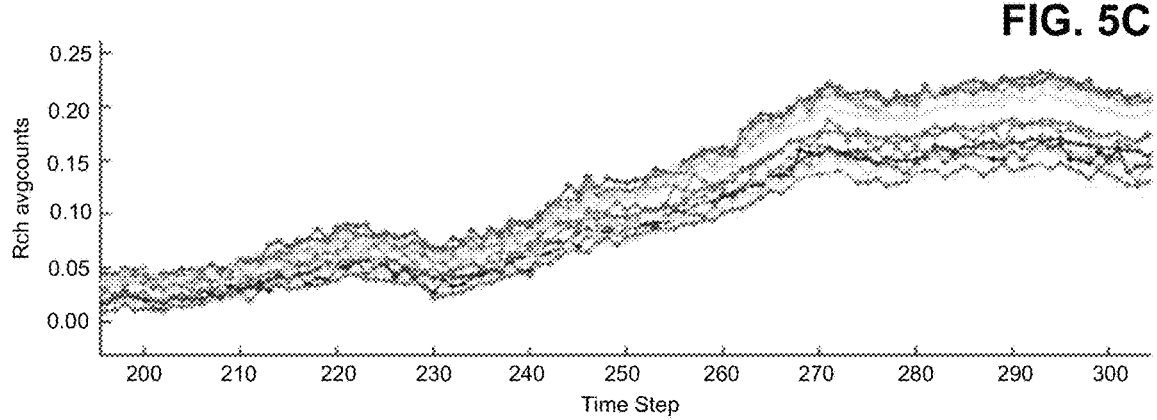
Figure 5D:
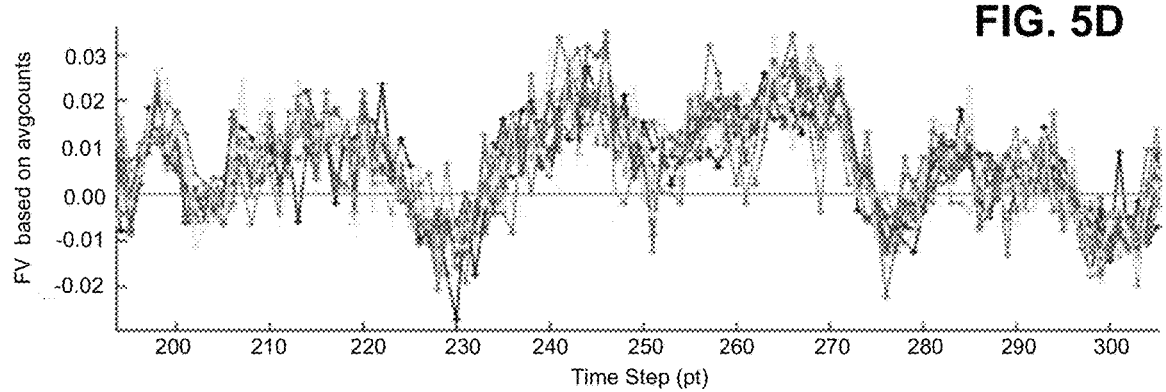

FIG. 5C is an example illustrating raw heartbeat data (in the form of relative count change of average counts) for the 14 wavelength channels during a time window from approximately time step 180 to approximately time step 320. Notably, the raw heartbeat data illustrated in FIG. 5C has a baseline with a significantly positive slope. In some implementations, as described above, feature vectors can be generated for each of the wavelength channels. FIG. 5D is an example illustrating a result of transforming the raw heartbeat data, associated with each of the 14 wavelength channels, to a respective moving quarter-period slopes feature vector. As shown in FIG. 5D, positive and negative phases of the feature vectors are relatively identifiable (e.g., as compared to the raw heartbeat data). Thus, as described above, feature vector transformation may allow heartbeat cycle data to be determined by heartbeat cycle data device 210. In some implementations, as described above, heartbeat cycle data device 210 may correct gaps resulting from the positively sloped baseline in the manner described above (e.g., after generating an average feature vector).

As indicated above, FIGS. 5A-5D are provided merely as examples. Other examples may differ from what is described with regard to FIGS. 5A-5D.

Figure 6:
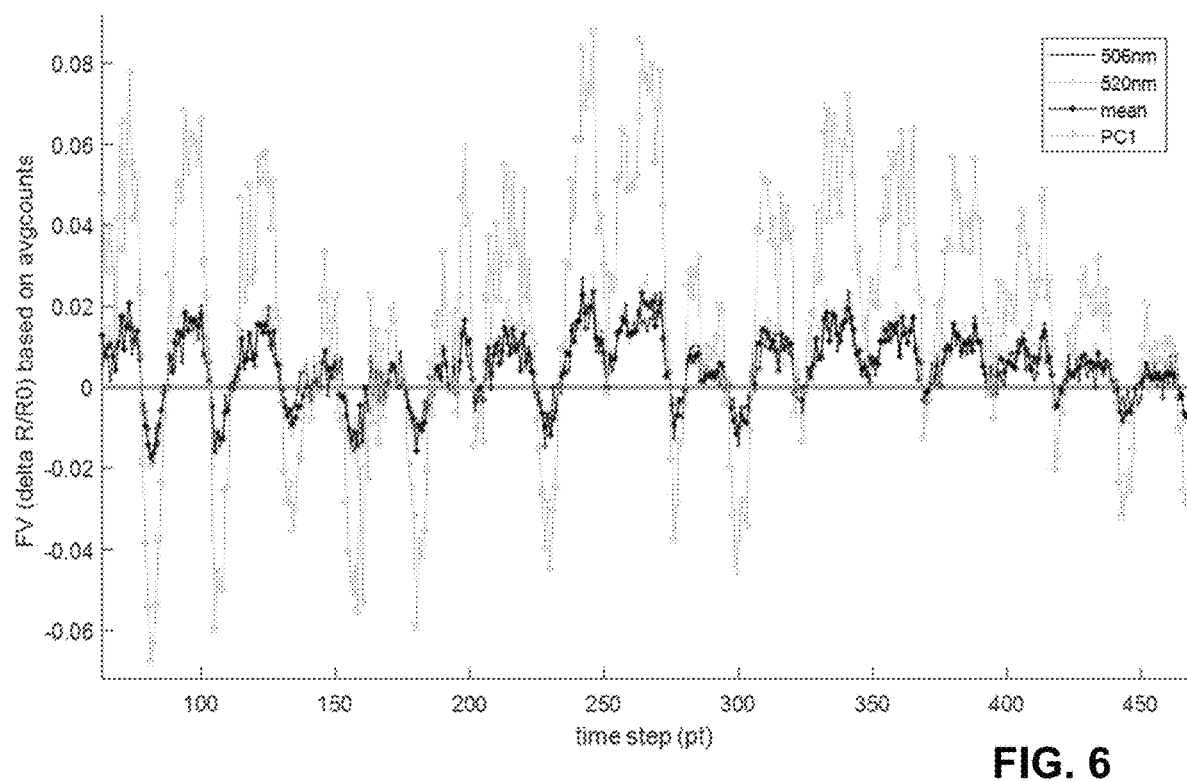
FIG. 6 is a diagram illustrating an example of an average feature vector generated based on a principal component analysis of a set of selected feature vectors, as described herein.

FIG. 6 is a diagram illustrating an example of an average feature vector generated based on a principal component analysis of a set of selected feature vectors, as described herein. As shown in FIG. 6, in this example, a feature vector corresponding to a 506 nanometer (nm) wavelength channel, a feature vector corresponding to a 520 nm wavelength channel, and a feature vector corresponding to a mean of the set of selected feature vectors (e.g., a set of selected feature vectors that includes the feature vectors corresponding to the 506 nm and 520 nm channels) have values that range between approximately −0.02 and approximately 0.02 in a given time window. As further shown, an average feature vector (PC1) generated using a PCA of the set of selected feature vectors has a value that ranges between approximately −0.06 and 0.08 in the given time window.

As illustrated by FIG. 6, generating the average feature vector (e.g., PC1) using a PCA provides a signal with a significantly higher SNR (e.g., as compared to an individual one of the set of selected feature vectors or a mean of the set of selected feature vectors) and, therefore, allows positive and negative phases to be more readily identified in association with determining heartbeat cycle data in the manner described above.

As indicated above, FIG. 6 is provided merely as an example. Other examples may differ from what is described with regard to FIG. 6.

Figure 7A:
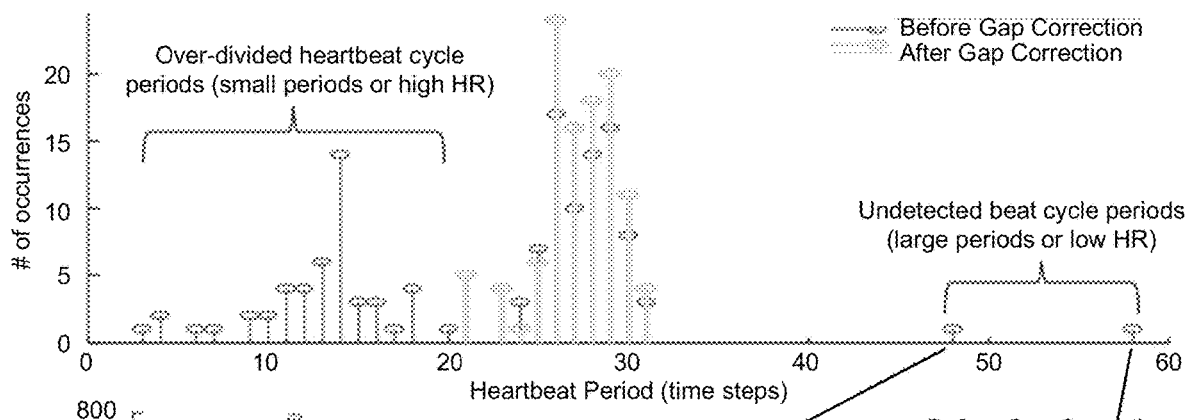
FIGS. 7A and 7B are diagrams illustrating an example effect of heartbeat data gap correction in initial heartbeat cycle data, as described herein.
Figure 7B:
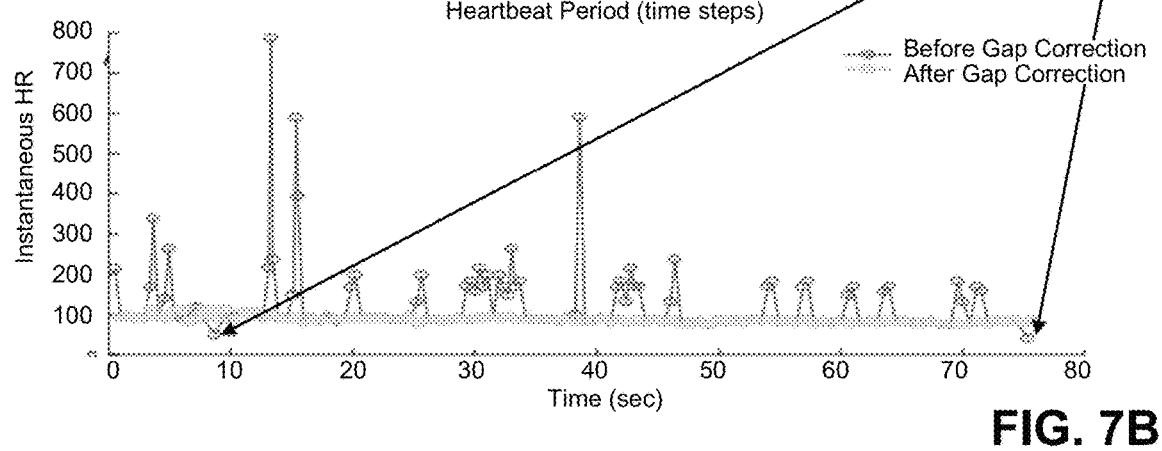

FIGS. 7A and 7B are diagrams illustrating an example effect of heartbeat data gap correction in initial heartbeat cycle data, as described herein. FIG. 7A illustrates an example of numbers of occurrences of different heartbeat periods before and after gap correction during a given time window, and FIG. 7B illustrates an example of determined instantaneous heart rates before and after gap correction during the given time window.

As shown in FIG. 7A, before gap correction, a number of over-divided heartbeat cycle periods (e.g., heartbeat cycle periods with periods of less than approximately 20 time steps) and undetected heartbeat cycle periods are present. As further shown, after gap correction, these gaps are removed (e.g., such that all heartbeat cycles have a period that is between approximately 20 and approximately 32 time steps).

Similarly, as shown in FIG. 7B, before gap correction, the instantaneous heart rate includes numerous positive spikes (e.g., above approximately 150 beats per minute) resulting from the over-divided heartbeat cycle periods, and negative spikes resulting from the undetected heartbeat cycle periods. As further shown, after gap correction, these spikes are removed (e.g., such that the instantaneous heart rate does not include sudden significant increases or decreases).

As indicated above, FIGS. 7A and 7B are provided merely as examples. Other examples may differ from what is described with regard to FIGS. 7A and 7B.

Figure 8:
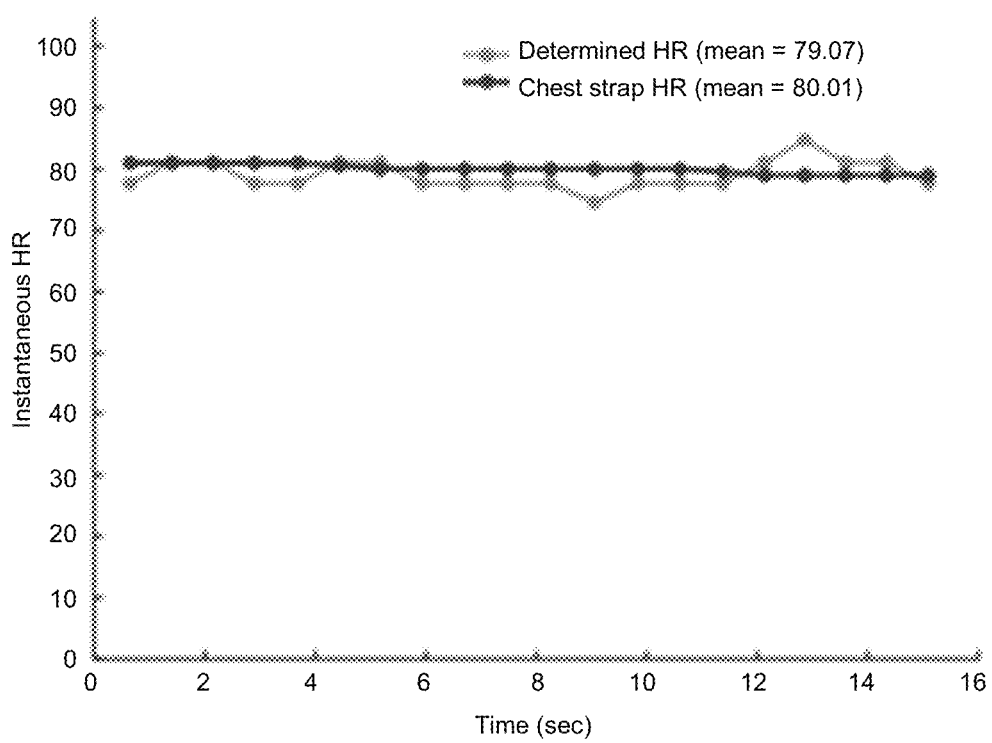
FIG. 8 is a diagram illustrating an example of instantaneous heart rates determined based on final heartbeat cycle data, as described herein.

FIG. 8 is a diagram illustrating an example of instantaneous heart rates determined based on final heartbeat cycle data, a described herein. As shown in FIG. 8, an instantaneous heart rate determined based on final heartbeat cycle data, as described herein, may approximately match (e.g., within a few beats per minute) an instantaneous heart rate determined in a conventional chest strap heart rate monitor (which is known to be relatively accurate). Notably, further improvement may result from smoothing of the determined instantaneous heart rate (e.g., using a moving window average) and, therefore, a closer match than that illustrated in FIG. 8 can be achieved. In either case, as illustrated in FIG. 8, the final heartbeat cycle data, determined in the manner described herein, may allow for a biometric monitoring action to be performed with an acceptable accuracy and/or reliability.

As indicated above, FIG. 8 is provided merely as an example. Other examples may differ from what is described with regard to FIG. 8.

Some implementations described herein allow heartbeat cycle data device 210 to determine, based on raw heartbeat data collected by multispectral sensor device 205, heartbeat cycle data based on which a biometric monitoring action can be performed. More specifically, some implementations described herein allow heartbeat cycle data device 210 to process the raw heartbeat data in order to determine the heartbeat cycle data, thereby allowing a biometric monitoring action that uses the heartbeat cycle data to provide a comparatively more accurate and/or comparatively more reliable result (e.g., as compared to using raw heartbeat data in association with performing the biometric monitoring action).

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like, depending on the context.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
    identifying, by a device and based on raw heartbeat data, a plurality of feature vectors;
    identifying, by the device, one or more selected feature vectors, from the plurality of feature vectors, based on a square of correlation coefficients associated with a pair of the plurality of feature vectors;
    determining, by the device, final heartbeat cycle data based on the one or more selected feature vectors; and
    providing, by the device, information associated with the final heartbeat cycle data.

2. The method of claim 1, further comprising:
    receiving the raw heartbeat data from a multispectral sensor device,
        wherein the multispectral sensor device is positioned relative to a skin surface of a subject.

3. The method of claim 1, further comprising:
    receiving the raw heartbeat data from a multispectral sensor device,
        wherein the device is integrated with the multispectral sensor device in a same housing.

4. The method of claim 1, further comprising:
    receiving the raw heartbeat data from a multispectral sensor device,
        wherein the device is remotely located from the multispectral sensor device.

5. The method of claim 1, wherein a feature vector, of the one or more selected feature vectors, corresponds to a wavelength channel.

6. The method of claim 1,
    wherein identifying the one or more selected feature vectors comprises:
        identifying the one or more selected feature vectors, from the plurality of feature vectors, that correspond to a set of squares of correlation coefficients that satisfy a threshold, and wherein the set of squares of correlation coefficients includes the square of correlation coefficients.

7. A device, comprising:
one or more memories; and
one or more processors, coupled to the one or more memories, configured to:
identify, based on raw heartbeat data, a plurality of feature vectors;
identify one or more selected feature vectors, from the plurality of feature vectors, that correspond to a set of squares of a plurality of squares of correlation coefficients associated with the plurality of feature vectors;
determine final heartbeat cycle data based on the one or more selected feature vectors; and
provide information associated with the final heartbeat cycle data.

8. The device of claim 7, wherein the one or more processors are further configured to:
receive raw heartbeat data from a multispectral sensor device that is positioned relative to a skin surface of a subject.

9. The device of claim 7, wherein the one or more processors are further configured to:
receive the raw heartbeat data from a multispectral sensor device that is integrated with the device in a same housing.

10. The device of claim 7, wherein the one or more processors are further configured to:
receive the raw heartbeat data from a multispectral sensor device that is remotely located from the device.

11. The device of claim 7, wherein a feature vector, of the one or more selected feature vectors, corresponds to a wavelength channel.

12. The device of claim 7, wherein a square of correlation coefficients, of the set of squares, is associated with a pair of the plurality of feature vectors.

13. The device of claim 7, wherein the one or more processors, to identify the one or more selected feature vectors, are configured to:
identify the one or more selected feature vectors, from the plurality of feature vectors, based on the set of squares satisfying a threshold.

14. A non-transitory computer-readable medium storing a set of instructions, the set of instructions comprising:
one or more instructions that, when executed by one or more processors of a device, cause the device to:
identify, based on raw heartbeat data, a plurality of feature vectors;
identify one or more selected feature vectors, from the plurality of feature vectors, based on a square of correlation coefficients associated with a pair of the plurality of feature vectors;
determine heartbeat cycle data based on the one or more selected feature vectors; and
provide information associated with the heartbeat cycle data.

15. The non-transitory computer-readable medium of claim 14, wherein the raw heartbeat data is from a multispectral sensor device that is positioned relative to a skin surface of a subject.

16. The non-transitory computer-readable medium of claim 14, wherein the device is integrated with a multispectral sensor device in a same housing.

17. The non-transitory computer-readable medium of claim 14, wherein the device is remotely located from a multispectral sensor device that obtains the raw heartbeat data.

18. The non-transitory computer-readable medium of claim 14, wherein a feature vector, of the one or more selected feature vectors, corresponds to a wavelength channel.

19. The non-transitory computer-readable medium of claim 14,
wherein the one or more selected feature vectors are identified further based on a different square of correlation coefficients of a set of squares of correlation coefficients that includes the square of correlation coefficients, and
wherein the set of squares of correlation coefficients satisfy a threshold.

20. The method of claim 1, wherein providing the information associated with the final heartbeat cycle data comprises:
providing the final heartbeat cycle data to a different device that is configured to perform vital sign monitoring.

* * * * *